US008999734B2

(12) United States Patent
McAndrew et al.

(10) Patent No.: US 8,999,734 B2
(45) Date of Patent: Apr. 7, 2015

(54) CYCLIC AMINO COMPOUNDS FOR LOW-K SILYLATION

(75) Inventors: James J. F. McAndrew, Chadds Ford, PA (US); Curtis Anderson, Downingtown, PA (US); Christian Dussarrat, Wilmington, DE (US)

(73) Assignee: American Air Liquide, Inc., Fremont, CA (US)

( * ) Notice: Subject to any disclaimer, the term of this patent is extended or adjusted under 35 U.S.C. 154(b) by 947 days.

(21) Appl. No.: 12/721,362

(22) Filed: Mar. 10, 2010

(65) Prior Publication Data

US 2010/0233829 A1    Sep. 16, 2010

Related U.S. Application Data

(60) Provisional application No. 61/158,995, filed on Mar. 10, 2009.

(51) Int. Cl.
*H01L 21/00* (2006.01)
*C07F 7/10* (2006.01)
*H01L 21/02* (2006.01)

(52) U.S. Cl.
CPC ............ *C07F 7/10* (2013.01); *H01L 21/02343* (2013.01); *H01L 21/02359* (2013.01)

(58) Field of Classification Search
None
See application file for complete search history.

(56) References Cited

U.S. PATENT DOCUMENTS

| 3,940,402 A | | 2/1976 | Middleton |
| 4,808,511 A | * | 2/1989 | Holmes ........................ 430/325 |
| 5,399,200 A | * | 3/1995 | Stauffer ........................ 118/726 |
| 5,429,673 A | | 7/1995 | Peterson et al. |
| 5,922,449 A | | 7/1999 | Revis |
| 6,208,014 B1 | | 3/2001 | Wu et al. |
| 6,312,793 B1 | | 11/2001 | Grill et al. |
| 6,395,651 B1 | | 5/2002 | Smith et al. |
| 6,475,904 B2 | | 11/2002 | Okoroanyanwu et al. |
| 6,479,110 B2 | | 11/2002 | Grill et al. |
| 6,479,374 B1 | | 11/2002 | Ioka et al. |
| 6,495,906 B2 | | 12/2002 | Smith et al. |
| 6,518,205 B1 | | 2/2003 | Wu et al. |
| 6,756,323 B2 | | 6/2004 | Grill et al. |
| 6,953,984 B2 | | 10/2005 | Grill et al. |
| 7,029,826 B2 | | 4/2006 | Hacker et al. |
| 7,030,468 B2 | | 4/2006 | Gates et al. |
| 7,049,427 B2 | | 5/2006 | Hanummappa et al. |

(Continued)

FOREIGN PATENT DOCUMENTS

| EP | 2 154 141 | 8/2009 |
| JP | 5 228372 | 9/1993 |

(Continued)

OTHER PUBLICATIONS

Attached data sheet of N-trimethylsilylpiperidine and N-trimethylsilylpyrrolidine compounds as generated by ChemDraw Ultra software.*

(Continued)

*Primary Examiner* — Yasser A Abdelaziez
(74) *Attorney, Agent, or Firm* — Patricia E. McQueeney; Allen E. White

(57) ABSTRACT

Disclosed herein are mono-functional silylating compounds that may exhibit enhanced silylating capabilities. Also disclosed are method of synthesizing and using these compounds. Finally methods to determine effective silylation are also disclosed.

15 Claims, 1 Drawing Sheet

(56) References Cited

U.S. PATENT DOCUMENTS

| | | | |
|---|---|---|---|
| 7,083,991 B2 | 8/2006 | Gaynor | |
| 7,176,144 B1 | 2/2007 | Wang et al. | |
| 7,179,758 B2 | 2/2007 | Chakrapani et al. | |
| 7,208,389 B1 | 4/2007 | Tipton et al. | |
| 7,223,704 B2 | 5/2007 | Weber | |
| 7,282,458 B2 | 10/2007 | Gates et al. | |
| 7,288,292 B2 | 10/2007 | Gates et al. | |
| 7,312,524 B2 | 12/2007 | Gates et al. | |
| 7,345,000 B2 | 3/2008 | Kevwitch et al. | |
| 7,446,058 B2 | 11/2008 | Yang et al. | |
| 7,482,281 B2 | 1/2009 | Fujii et al. | |
| 7,500,397 B2 | 3/2009 | Weigel et al. | |
| 7,541,200 B1 | 6/2009 | Van Schravendijk et al. | |
| 7,553,769 B2 | 6/2009 | Toma et al. | |
| 7,687,913 B2 | 3/2010 | Chakrapani et al. | |
| 7,750,479 B2 | 7/2010 | Purushothaman et al. | |
| 7,795,740 B2 | 9/2010 | Yang et al. | |
| 7,799,703 B2 | 9/2010 | Kubota et al. | |
| 7,842,518 B2 | 11/2010 | Miyajima | |
| 7,851,232 B2 | 12/2010 | Van Schravendijk et al. | |
| 7,858,294 B2 | 12/2010 | Hacker et al. | |
| 7,902,077 B2 | 3/2011 | Asako et al. | |
| 7,915,159 B2 | 3/2011 | Bhanap et al. | |
| 7,915,181 B2 | 3/2011 | Fan et al. | |
| 2004/0077886 A1* | 4/2004 | Yamamoto | 549/523 |
| 2005/0095840 A1 | 5/2005 | Bhanap et al. | |
| 2005/0158884 A1* | 7/2005 | Gaynor | 438/4 |
| 2006/0068102 A1 | 3/2006 | Meiere | |
| 2006/0189133 A1* | 8/2006 | Dimitrakopoulos et al. | 438/687 |
| 2006/0216952 A1 | 9/2006 | Bhanap et al. | |
| 2007/0057235 A1 | 3/2007 | Teff et al. | |
| 2007/0077782 A1 | 4/2007 | Lee et al. | |
| 2007/0249156 A1* | 10/2007 | Bonilla et al. | 438/622 |
| 2008/0057728 A1 | 3/2008 | Shimura et al. | |
| 2008/0241499 A1* | 10/2008 | Sinapi et al. | 428/304.4 |
| 2008/0283972 A1 | 11/2008 | Muh et al. | |
| 2009/0001046 A1 | 1/2009 | Kubota et al. | |
| 2009/0014414 A1 | 1/2009 | Tomioka et al. | |
| 2009/0075472 A1 | 3/2009 | Arnold et al. | |
| 2009/0075490 A1 | 3/2009 | Dussarrat | |
| 2009/0146145 A1 | 6/2009 | Sasahara et al. | |
| 2009/0286399 A1 | 11/2009 | Fujii et al. | |
| 2009/0305480 A1 | 12/2009 | Sasahara et al. | |
| 2009/0311859 A1 | 12/2009 | Bonilla et al. | |
| 2010/0041243 A1 | 2/2010 | Cheng et al. | |
| 2010/0050867 A1 | 3/2010 | Murata | |
| 2010/0062612 A1 | 3/2010 | Ishikawa | |
| 2010/0249445 A1 | 9/2010 | Yan et al. | |
| 2011/0003402 A1 | 1/2011 | Chakrapani et al. | |
| 2011/0020955 A1 | 1/2011 | DeYoung | |
| 2011/0053375 A1 | 3/2011 | Ishikawa et al. | |
| 2011/0092071 A1 | 4/2011 | Kinoshita et al. | |
| 2011/0111533 A1 | 5/2011 | Varadarajan et al. | |
| 2011/0115090 A1 | 5/2011 | Lin | |
| 2011/0117678 A1 | 5/2011 | Varadarajan et al. | |
| 2011/0120650 A1 | 5/2011 | Asako et al. | |

FOREIGN PATENT DOCUMENTS

| | | |
|---|---|---|
| WO | WO 95 10072 | 4/1995 |
| WO | WO 00 02233 | 1/2000 |
| WO | WO 2002 027063 | 4/2002 |
| WO | WO 2006 049595 | 5/2006 |

OTHER PUBLICATIONS

McMurtrey, K. "Reaction of silica gel with trimethylsilyl donors under conditions useful for end-capping HPLC bonded phase packings," Journal of Liquid Chromatography, 11(16), 3375-3384 (1988).

"The International Technology Roadmap for Semiconductors", 2007, Interconnect.

International Search Report and Written Opinion for PCT/US2010/026865, Oct. 14, 2010.

* cited by examiner

CYCLIC AMINO COMPOUNDS FOR LOW-K SILYLATION

CROSS REFERENCE TO RELATED APPLICATIONS

The present application claims the benefit of U.S. Provisional Application Ser. No. 61/158,995 filed Mar. 10, 2009, incorporated herein by reference in its entirety for all purposes.

BACKGROUND

Insulating films with low dielectric constant (low-k) are critically required for semiconductor manufacturing (see for example International Technology Roadmap for Semiconductors, Interconnect chapter, 2007 edition). Low-k films are usually created by introducing pores containing air or other gases, which have a dielectric constant close to 1, into a matrix material with dielectric constant in the range 2.0-3.0. The effective dielectric constant of the resulting porous film is typically 2.2 or less.

The low-k matrix material is typically a hydrogenated carbon-doped silicon oxide (SiCOH), wherein the free surfaces are terminated with methyl groups ($CH_3$) bound to silicon. Processing steps, such as etching or chemical mechanical polishing, effectively remove the methyl terminations, leaving either dangling bonds or hydroxyl groups (Si—OH). As a result, the film becomes more hydrophilic and can readily absorb moisture. This in turn leads to an increase in the dielectric constant, the degree of which depends on the severity of the damaging process.

Another effect of carbon depletion is its impact on critical dimensions. For instance, the etching process used to form a trench through the low-k film would tend to leave the trench walls depleted of carbon. In subsequent wet stripping or cleaning processes the trench can be significantly broadened, a problem that becomes even more critical as feature size is reduced.

One solution to this problem is to repair the film by restoring carbon atoms with a silylating agent. Several families of compounds have been used as silylating agents for low-k repair, particularly alkoxysilanes, chlorosilanes, and aminosilanes. Of these, alkoxysilanes are the least reactive, but have the advantage that their chemistry is completely compatible with the SiCOH film. Chlorosilanes are difficult to handle due to their high reactivity with atmospheric moisture, as well as their tendency to form hydrochloric acid (HCl) as a silylation reaction byproduct. HCl may be problematic for metallic films present elsewhere in the circuit.

The use of aminosilanes for low-k repair has been demonstrated in several sources. In U.S. Pat. No. 6,395,651 to Smith et al. claim a nanoporous silica dielectric film treated by and a process for treating the same with a surface modification agent, such as hexamethyldisilazane (HMDS). The authors demonstrate that various exposure methods of exemplary films to HMDS resulted in a hydrophobic film surface, whereas an untreated film remained hydrophilic based on water droplet contact angle experiments. In a further example, Hacker et al. in U.S. Pat. No. 7,029,826 claim a method of imparting hydrophobic properties to a damaged silica dielectric film by contacting the damaged film with a surface modification agent, such as methyltriacetoxysilane (MTAS). U.S. Pat. No. 7,345,000 claims a method of treating a dielectric film by exposing the film to a treating compound and an alkyl silane, wherein the treating compound preferably includes HMDS, chlorotrimethylsilane (TMCS), trichloromethylsilane (TCMS), and combinations of these.

In U.S. Pat. No. 7,179,758, assigned to IBM (International Business Machines Corporation), compounds with two functional groups are considered as preferred over their mono-functional analogs because, in theory, a di-functional molecule could react with two neighboring Si—OH groups and mono-functional compounds can only react with one Si—OH. However, it is also suggested that a post-silylation annealing step is used to "condense" remaining Si—OH groups, allowing new Si—O—Si bonds to form. IBM's exemplary treatment processes suggest that bis(dimethylamino)dimethylsilane (BDMADMS), a di-functional molecule, provides superior hydrophobic properties compared to HMDS, a mono-functional molecule.

Considering the above references either separately or in conjunction, one can see that reaction compounds having at least one Si—N bond at the active site appear to be the most effective for surface modifications of silica-based films. This concept was concluded in the work of K. McMurtrey in the Journal of Liquid Chromatography, 11(16), 3375-3384 (1988), wherein several trimethylsilyl-(TMS) donors were compared in terms of their reactivity with silanol groups at the surface of silica gel particles. The results of this work suggest that trimethylsilyl-imidazole (TMSI), having a nitrogen-containing ring functional group, was more effective for this surface reaction compared to all of the above-mentioned compounds, as well as others known in the art such as trimethylsilyldimethylamine (TMSDMA). While the granted patents referenced above indeed claim TMSI as a treating compound for either surface modification or dielectric repair, the field of nitrogen-containing ring molecules remains unexplored in the art to date.

SUMMARY

Disclosed is a silylation compound of the formula $R_3SiL$, wherein each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom. The silylation compound has a total concentration of metal contaminants of less than 10 ppmw. The disclosed compound may include one or more of the following aspects:
 the compound may be selected from the group consisting of trimethylsilylpyrrolidine, trimethylsilylpyrazole, trimethylsilyl-1,2,3-triazole, trimethylsilylpiperidine, and trimethylsilyl-4-methylpiperazine;
 a total concentration of metal contaminants of less than 1 ppmw;
 a boiling point of less than approximately 200° C.; and/or
 a boiling point between approximately 100° C. and approximately 200° C.

Also disclosed is a silylation chemistry delivery device comprising a canister having an inlet conduit and an outlet conduit and containing a silylating agent having a formula $R_3SiL$, wherein each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom. The disclosed device may include one or more of the following aspects:
 the silylating agent having a total concentration of metal contaminants of less than 10 ppmw.

the silylating agent being selected from the group consisting of trimethylsilylpyrrolidine, trimethylsilylpyrazole, trimethylsilyl-1,2,3-triazole, trimethylsilylpiperidine, and trimethylsilyl-4-methylpiperazine;

an end of the inlet conduit end located above a surface of the silylating agent and an end of the outlet conduit located below the surface of the silylating agent; and an end of the inlet conduit end located below a surface of the silylating agent and an end of the outlet conduit located above the surface of the silylating agent.

Also disclosed is a method of repairing a dielectric film in which the dielectric film is introduced into a chamber. A repair agent is introduced into the chamber, the repair agent having a formula $R_3SiL$, wherein each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom. The repair agent is contacted with the dielectric film. The disclosed method may include one or more of the following aspects:

heating the dielectric film after introduction into the chamber and prior to introduction of the repair agent;

allowing the repair agent to react with the dielectric film for a suitable length of time following the contacting step;

annealing the dielectric film following the repair agent reaction step;

the repair agent being selected from the group consisting of trimethylsilylpyrrolidine, trimethylsilylpyrazole, trimethylsilyl-1,2,3-triazole, trimethylsilylpiperidine, and trimethylsilyl-4-methylpiperazine; and the repair agent having a total concentration of metal contaminants of less than 10 ppmw.

NOTATION AND NOMENCLATURE

Certain abbreviations, symbols, and terms are used throughout the following description and claims and include: the abbreviation "HMDS" refers to hexamethyldisilazane; the abbreviation "MTAS" refers to methyltriacetoxysilane; the abbreviation "TMCS" refers to chlorotrimethylsilane; the abbreviation "TCMS" refers to trichloromethylsilane; the abbreviation "BDMADMS" refers to bis(dimethylamino) dimethylsilane; the abbreviation "TMS" refers to trimethylsilyl [$(CH_3)_3$—Si—]; the abbreviation "TMSI" refers to trimethylsilylimidazole; the abbreviation "TMSDMA" refers to trimethylsilyldimethylamine; the abbreviation "ppmw" refers to parts per million by weight; the abbreviation "ppbw" refers to parts per billion by weight; the abbreviation "MIM" refers to Metal Insulator Metal (a structure used in capacitors); the abbreviation "DRAM" refers to dynamic random access memory; the abbreviation "FeRAM" refers to ferroelectric random access memory; the abbreviation "CMOS" refers to complementary metal-oxide-semiconductor; the abbreviation "UV" refers to ultraviolet; the abbreviation "RF" refers to radiofrequency; the abbreviation "BOE" refers to a buffered oxide etch; the abbreviation "ER" refers to etch rate; and the terms "mono-functional silylating compound", "repair agent", "repair chemical", "silylating agent", "silylation compound", and "silylating compound" are used interchangeably to refer to compounds having the formula $R_3SiL$, where each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
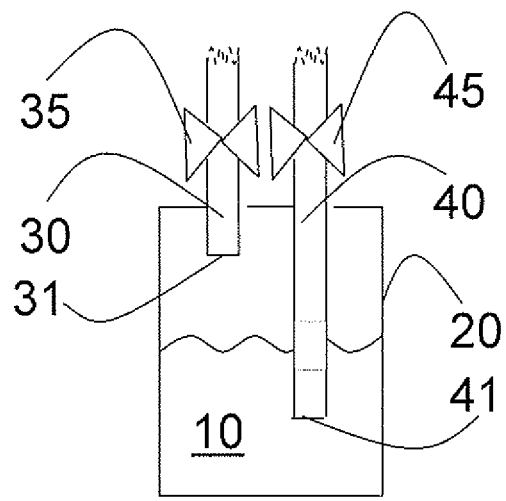
FIG. 1 is a side view of one embodiment of the silylation chemistry delivery device disclosed herein.

Disclosed herein are non-limiting embodiments of methods, apparatus and compounds which may be used in the manufacture of semiconductor, photovoltaic, LCD-TFT, or flat panel type devices.

In a silylation process, the use of di-functional compounds may not be beneficial, and in fact may leave reactive terminations in the film that will either increase the dielectric constant, or leave a pathway for significant moisture uptake.

Our preliminary studies suggest that mono-functional silylating compounds are similar or better for restoration of the dielectric constant than their multi-functional analogs. Initial tests have been performed using the following compounds having one, two, and three reactive groups, respectively:

Trimethylethoxysilane
Dimethyldiethoxysilane
Methyltriethoxysilane

The damaged films were repaired by exposing them to each of the three compounds in the vapor phase in a vacuum tube-furnace system. At least for these three molecules, the results suggest having a single reactive group provides similar restoration of the dielectric constant as the two- and three-reactive species.

Our results contrast with those in U.S. Pat. No. 7,179,758 (Chakrapani) and U.S. Pat. No. 7,029,826 (Hacker), which indicate that multi-functional silylating agents provide better results than mono-functional agents. Without wishing to be bound by theory, Applicants speculate that the substrates investigated in previous studies were very heavily damaged with abundant silanols in close proximity to one another on the surface, whereas more realistic surfaces may be less damaged with relatively isolated silanols, and therefore more effectively repaired by mono-functional repair agents.

Other mono-functional silylating compounds that may exhibit enhanced silylating capabilities have the formula $R_3SiL$, where each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom. Preferably, at least two of the R are methyl.

Without being bound by theory, Applicants believe that the ring structure of these mono-functional silylating compounds lowers steric hindrance. The ring constrains the hydrocarbon groups bound to the nitrogen from rotating into a position where they might shield the nitrogen atom from interaction with silanol groups on the surface, thereby rendering these molecules highly effective as silylation compounds. Preferably, the nitrogen-containing ring is saturated.

However, notwithstanding the theory above, not all nitrogen-containing ring structures prove effective as the L component. As demonstrated in Table 2 infra, neither pyrrole nor 1,2,4-triazole provide suitable repair to damaged films. Applicants have not yet discovered a suitable theory that explains the lack of effect of these molecules.

Exemplary preferred molecules include:

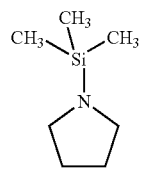

Trimethylsilypyrrolidine

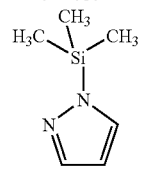

Trimethylsilypyrazole

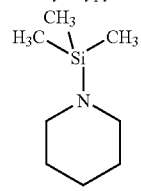

Trimethylsilylpiperidine

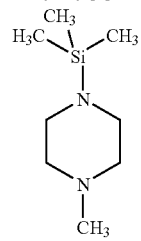

Trimethylsilyl-4-methylpiperzaine

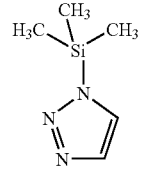

Trimethylsilyl-1,2,3-triazole

Preferably, the mono-functional silylating compound has a high volatility in order to facilitate its delivery to a treatment chamber in the vapor phase for vapor phase treatment. If liquid phase treatment is used, volatility should be low enough to enable easy delivery as a liquid but high enough to facilitate the removal of any unreacted silylating agent by evaporation after treatment. For vapor phase delivery, preferably, the boiling point of the silylating agent is less than approximately 200° C. For liquid phase delivery, the boiling point is preferably between approximately 100° C. and approximately 200° C. For example, the boiling point of trimethylsilylpiperidine is approximately 166° C., that of tri-methylsilylpyrrolidine is approximately 144° C., and that of trimethylsilyl 1,2,3-triazole is approximately 163° C. (all boiling points at atmospheric pressure), all of which are within the preferred range.

Method of Synthesis

The disclosed molecules may be synthesized by conventional methods, such as the following scheme:

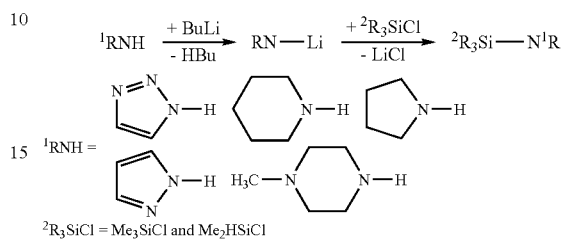

The above reactions may be carried out under an inert atmosphere, for example under flowing dry nitrogen. The starting materials, $^1$RNH and $^2$R$_3$Si—N$^1$R, are available commercially.

Preferred Purity

In order to avoid contamination of the dielectric film to be repaired, it is important that the mono-functional silylating compound be free of contaminants, especially metal contaminants which are known to be particularly undesirable in dielectric films. A metal contaminant includes elements in group IA-IIIA or I-VIIIB of the periodic table. Preferably, the total concentration of metal contaminants in the compound should be less than 10 ppmw (parts per million by weight), more preferably, less than 1 ppmw. For example, a target metal content specification is illustrated at 130 ppbw (parts per billion by weight) in Table 1:

TABLE 1

Exemplary Target Metal Content

| Element* | | Specification (ppb) | Unit |
|---|---|---|---|
| Al | Aluminum | 1 | ppbw |
| As | Arsenic | 1 | ppbw |
| Ag | Silver | 1 | ppbw |
| Au | Gold | 1 | ppbw |
| B | Boron | 5 | ppbw |
| Ba | Barium | 1 | ppbw |
| Bo | Beryllium | 1 | ppbw |
| Bi | Bismuth | 1 | ppbw |
| Ca | Calcium | 1 | ppbw |
| Co | Cobalt | 1 | ppbw |
| Cr | Chromium | 1 | ppbw |
| Cu | Copper | 1 | ppbw |
| Fe | Iron | 1 | ppbw |
| Ga | Gallium | 1 | ppbw |
| K | Potassium | 1 | ppbw |
| Li | Lithium | 1 | ppbw |
| Mg | Magnesium | 1 | ppbw |
| Mn | Manganese | 1 | ppbw |
| Na | Sodium | 1 | ppbw |
| Ni | Nickel | 1 | ppbw |
| P | Phosphorus | 100 | ppbw |
| Pb | Lead | 1 | ppbw |
| Sb | Antimony | 1 | ppbw |
| Sn | Tin | 1 | ppbw |
| Sr | Strontium | 1 | ppbw |
| Ti | Titanium | 1 | ppbw |
| Zr | Zirconium | 1 | ppbw |

The target metal content may generally be achieved by distillation using known methods. Metal components in the construction of the distillation system should be minimized, and leaks must be carefully excluded. A new distillation system will generally require conditioning by operation at 100% reflux before commencing collection of distilled product.

Silylation Chemistry Delivery Device

Figure 2:
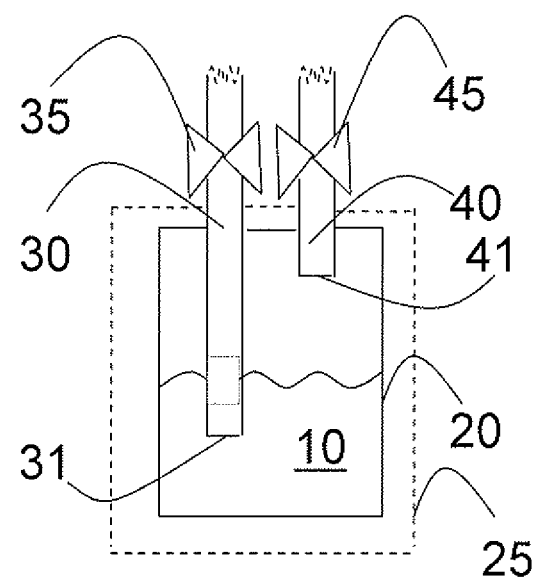
FIG. 2 is a side view of a second embodiment of the silylation chemistry delivery device disclosed herein.

The mono-functional silylating compounds may be delivered to a semiconductor processing tool by the disclosed silylation chemistry delivery devices. FIGS. 1 and 2 show two embodiments of the disclosed silylation chemistry device 1.

FIG. 1 is a side view of one embodiment of the silylation chemistry delivery device 1. In FIG. 1, the disclosed mono-functional silylating compounds 10 are contained within a container 20 having two conduits, an inlet conduit 30 and an outlet conduit 40. One of ordinary skill in the precursor art will recognize that the container 20, inlet conduit 30, and outlet conduit 40 are manufactured to prevent the escape of the gaseous mono-functional silylating compound 10, even at elevated temperature and pressure.

The container fluidly connects to other components of the semiconductor processing tool via valves 35 and 45. Preferably, the container 20, inlet conduit 30, valve 35, outlet conduit 40, and valve 45 are made of 316L EP or 304 stainless steel. However, one of ordinary skill in the art will recognize that other non-reactive materials may also be used in the teachings herein and that corrosive mono-functional silylating compounds 10 may require the use of more corrosion-resistant materials, such as Hastelloy or Inconel.

In FIG. 1, the end 31 of inlet conduit 30 is located above the surface 11 of the mono-functional silylating compound 10, whereas the end 41 of the outlet conduit 40 is located below the surface 11 of the mono-functional silylating compound 10. In this embodiment, the mono-functional silylating compound 10 is preferably in liquid form. An inert gas, including but not limited to nitrogen, argon, helium, and mixtures thereof, may be introduced into the inlet conduit. The inert gas pressurizes the container 20 so that the liquid mono-functional silylating compound 10 is forced through the outlet conduit 40 and to components in the semiconductor processing tool (not shown). The semiconductor processing tool may include a vaporizer which transforms the liquid mono-functional silylating compound 10 into a vapor, with or without the use of a carrier gas such as helium, argon, nitrogen or mixtures thereof, in order to deliver the vapor to a chamber where a wafer to be repaired is located and treatment occurs in the vapor phase. Alternatively, the liquid mono-functional silylating compound 10 may be delivered directly to the wafer surface as a jet or aerosol.

FIG. 2 is a side view of a second embodiment of the silylation chemistry delivery device 1. In FIG. 2, the end 31 of inlet conduit 30 is located below the surface 11 of the mono-functional silylating compound 10, whereas the end 41 of the outlet conduit 40 is located above the surface 11 of the mono-functional silylating compound 10. FIG. 2, also includes an optional heating element 25, which may increase the temperature of the mono-functional silylating compound 10. In this embodiment, the mono-functional silylating compound 10 may be in solid or liquid form. An inert gas, including but not limited to nitrogen, argon, helium, and mixtures thereof, is introduced into the inlet conduit. The inert gas bubbles through the mono-functional silylating compound 10 and carries a mixture of the inert gas and vaporized mono-functional silylating compound 10 to the outlet conduit 40 and on to the components in the semiconductor processing tool.

Both FIGS. 1 and 2 include valves 35 and 45. One of ordinary skill in the art will recognize that valves 35 and 45 may be placed in an open or closed position to allow flow through conduits 30 and 40, respectively. Either the apparatus 1 in FIG. 1 or 2, or a simpler apparatus having a single conduit terminating above the surface of any solid or liquid present, may be used if the mono-functional silylating compound 10 is in vapor form or if sufficient vapor pressure is present above the solid/liquid phase. In this case, the mono-functional silylating compound 10 is delivered in vapor form through the conduit 30 or 40 simply by opening the valve 35 in FIG. 1 or 45 in FIG. 2, respectively. The apparatus 1 may be maintained at a suitable temperature to provide sufficient vapor pressure for the mono-functional silylating compound 10 to be delivered in vapor form, for example by the use of an optional heating element 25.

While FIGS. 1 and 2 disclose two embodiments of the silylation chemistry delivery device 1, one of ordinary skill in the art will recognize that the inlet conduit 30 and outlet conduit 40 may both be located above or below the surface 11 of the mono-functional silylating compound 10 without departing from the disclosure herein. Furthermore, inlet conduit 30 may be a filling port. Finally, one of ordinary skill in the art will recognize that the disclosed mono-functional silylating compounds may be delivered to semiconductor processing tools using other delivery devices, such as the ampoules disclosed in WO 2006/059187 to Jurcik et al., without departing from the teachings herein.

Method of Repair

In the disclosed methods of repair, the disclosed molecules are contacted with a dielectric film to restore carbon atoms to the film. Those skilled in the art will appreciate that the method of treatment for a silica-based film described in this document is not limited by a specific set of conditions or closely defined hardware. A significant variance of sample exposure conditions, such as temperature, time, pressure, and flowrate, could be applied to the disclosed molecules without departing from the spirit of the disclosed method of treatment. Likewise, the apparatus used to expose a sample to the disclosed molecules may also vary without departing from the disclosed method.

The disclosed method of repairing a dielectric film comprises the steps of introducing into a chamber the damaged dielectric film and a repair agent having the formula $R_3SiL$, where each R is independently selected from the group consisting of H, methyl, and ethyl; L is a nitrogen-containing ring selected from the group consisting of 1,2,3-triazole, piperidine, 1-methylpiperazine, pyrrolidine, and pyrazole; and one nitrogen in the nitrogen-containing ring is bonded directly to the Si atom. The repair agent contacts the damaged dielectric film.

The chamber is used to control the sample exposure environment. The substrate and dielectric film may optionally be heated to a temperature by way of an external energy source, such as a conductive or radiative supply. The repair agent may be introduced into the chamber in either the liquid or vapor phase. The repair agent reacts with the dielectric film for a suitable length of time, such that the film properties are completely or partially restored. Optionally, the substrate and dielectric film may be annealed following the repair agent reaction step, by way of an external energy source, such as a conductive or radiative supply.

The dielectric film is disposed on a substrate. The dielectric film may be composed of at least Si, C, O, and H, and may have other elemental constituents incorporated. The substrate may include other layers in addition to the dielectric layer. Exemplary, but non-limiting reference to the deposition processes disclosed in U.S. Pat. Nos. 6,312,793, 6,479,110, 6,756,323, 6,953,984, 7,030,468, 7,049,427, 7,282,458, 7,288,292, and 7,312,524 and U.S. Pat. App. Pub. No. 2007/0057235 is incorporated herein by reference. For example, U.S. Pat. App. Pub. No. 2007/0057235 discloses a method of forming a layer of carbon-doped silicon oxide on a substrate. Similarly, U.S. Pat. Nos. 6,312,793, 6,479,110, 6,756,323, 7,030,468, 7,049,427, 7,282,458, 7,288,292, and 7,312,524 disclose the plasma enhanced chemical vapor deposition of a combination of precursors (also referred to as the hydrocarbon molecules or organic molecules). Common highlights of these processes are further described herein.

The substrate may be placed in the reaction chamber of a deposition tool. The precursor(s) used to form the dielectric film may be delivered directly as a gas to the reactor, delivered as a liquid vaporized directly within the reactor, or transported by an inert carrier gas including, but not limited to, helium or argon. For example, the precursor(s) may be vaporized at a temperature between about 70° C. and about 110° C. in the presence of a carrier gas prior to introduction into the reaction chamber. Alternatively, the precursor(s) may be deposited in liquid form on the substrate, for example via a spin-on process.

The type of substrate upon which the dielectric film will be deposited will vary depending on the final use intended. In some embodiments, the substrate may include doped or undoped silicon optionally coated with a silicon oxide layer, in addition to oxides which are used as dielectric materials in MIM, DRAM, FeRam technologies or gate dielectrics in CMOS technologies (for example, $SiO_2$, SiON, or $HfO_2$ based materials, $TiO_2$ based materials, $ZrO_2$ based materials, rare earth oxide based materials, ternary oxide based materials, etc.), and metals that are used as conducting materials in such applications, such as for example, tungsten, titanium, tantalum, ruthenium, or copper. In other embodiments, the substrate may include copper interconnects and insulating regions, such as another low-k material, optionally coated with a sealing layer such as $SiO_2$ or SiN. Other examples of substrates upon which the insulating film may be coated include, but are not limited to, solid substrates such as metal substrates (for example, Ru, Al, Ni, Ti, Co, Pt and metal silicides, such as $TiSi_2$, $CoSi_2$, and $NiSi_2$); metal nitride containing substrates (for example, TaN, TiN, WN, TaCN, TiCN, TaSiN, and TiSiN); semiconductor materials (for example, Si, SiGe, GaAs, InP, diamond, GaN, and SIC); insulators (for example, $SiO_2$, $Si_3N_4$, $HfO_2$, $Ta_2O_5$, $ZrO_2$, $TiO_2$, $Al_2O_3$, and barium strontium titanate); or other substrates that include any number of combinations of these materials. The actual substrate utilized will also depend upon the dielectric film utilized.

The precursor(s) used to form the film are introduced into the film deposition chamber and contacted with the substrate to form an insulating layer on at least one surface of the substrate. The film deposition chamber may be any enclosure or chamber of a device in which deposition methods take place, such as, without limitation, a parallel plate-type reactor, a cold-wall type reactor, a hot-wall type reactor, a single-wafer reactor, a multi-wafer reactor, or other such types of deposition systems.

As discussed in more detail in the incorporated prior art, the film may subsequently be rendered porous by additional processing to reduce the dielectric constant of the insulating layer. Such processing includes, but is not limited to, annealing, UV light, or electron beam.

Based on the disclosure herein and in the references incorporated by reference, one of ordinary skill in the art would be able to easily select appropriate values for the process variables controlled during deposition of the films, including RF power, precursor mixture and flow rate, pressure in reactor, and substrate temperature.

The substrate and film structure may remain in the deposition chambers described above during the performance of the remaining steps of the disclosed methods. Alternatively, the substrate and film structure may be introduced into another apparatus that is used to control the sample exposure environment, such as the evaluation system described below.

The substrate and film may optionally be heated to an elevated temperature by way of an external energy source, such as a conductive or radiative supply. Depending upon the mono-functional silylating compound utilized, heat may assist with the silylation reaction. For example temperatures ranging from approximately 100° C. to approximately 400° C., preferably approximately 200° C. to approximately 300° C., may prove beneficial in certain circumstances. However, under other circumstances, the mono-functional silylating compound may decompose at elevated temperatures, and room temperature operation, for example approximately 20° C. to approximately 30° C., may therefore be optimal without requiring additional heating.

The silylation compound may be introduced into the chamber and transported to the substrate and film structure in either the liquid or vapor phase, such that the silylation compound is in contact with the film, allowing the compound to react with the film for a suitable length of time, such that the film properties are completely or partially restored. The silylation compound may be delivered directly as a gas to the apparatus, delivered as a liquid vaporized directly within the apparatus, or transported by an inert carrier gas including, but not limited to, nitrogen, helium, argon, or combinations thereof. Preferably, the silylation compound is vaporized at a temperature between approximately 20° C. to approximately 150° C., more preferably between approximately 70° C. and approximately 110° C., in the presence of a carrier gas prior to introduction into the apparatus.

Alternatively, the silylation compound may be in contact with the film in a liquid phase. This may be achieved via a liquid bath into which the substrate and film are placed for a suitable length of time, such that the film properties are completely or partially restored. Another alternative may be to introduce the liquid silylation compound into the treatment chamber and deliver it to the film by a jet, stream, or spray, optionally in a spin-on process.

The silylation compound reacts with the film for a suitable length of time between approximately 5 seconds and approximately 3 hours, more preferably between approximately one minutes and approximately one hour, and even more preferably between approximately one minute and approximately five minutes. After the silylation compound reacts with the film, the film properties are completely or partially restored, as indicated by improvement of the depth and etch rate parameters described in further detail below.

The substrate and film structure may optionally be annealed following the silylation compound reaction step by way of an external energy source, such as a conductive or radiative supply. Annealing may help remove remaining unreacted silanols. However, if the compound utilized is capable of removing a large portion of the unreacted silanols, an annealing step may not be necessary. The annealing process may take place in the same apparatus.

Description of Evaluation System

The apparatus used to evaluate of the effectiveness of the disclosed silylation compounds comprises a stainless steel vacuum tube furnace, fitted internally with a heat susceptor upon which the substrates to be treated are placed. Upstream of the tube furnace is the chemical delivery system, comprising a sealed bubbler containing the repair chemical and a purified nitrogen gas delivery system.

Prior to delivery of the repair chemical, the vacuum system is pumped to a base pressure, followed by a 5 minute continuous purge flow of nitrogen. Once the system reaches a steady temperature, the repair chemical is delivered to the substrate in the gas phase, either by a flow of nitrogen carrier gas under controlled flow rate and pressure conditions, or by filling the vacuum tube to a static pressure of the pure chemical vapor without nitrogen dilution.

Following the exposure of the substrate to the repair chemical, the system is purged for 5 minutes under steady flow of nitrogen, and filled to atmospheric pressure with nitrogen for removal of the substrates.

Evaluation of Repair

Following the treatment with a given silylation compound, several repair parameters were measured, which are expected to change significantly when compared to the damaged film state as a result of the repair process. In particular, two parameters are defined herein that are related to the film resistance to wet etching with a 600:1 buffered oxide etch (BOE) solution. In this testing, the wet etching process occurs after the film has been repaired and is not the damage causing process described in the specification. The 'Depth' parameter indicates the percentage of damaged film that is repaired by the given compound. By definition, an undamaged film is Depth=100%, while the damaged film is Depth=0%. Thus if a damaged film is wet etched to a depth of 50 nm after 1 hour of exposure to the etch solution and a repaired film is wet etched to a depth of 25 nm after the same exposure, Depth=50% for the repaired film.

The wet etch rate parameter, or ER, is measured between 12 and 24 minutes of wet etching in the 600:1 BOE solution, reported in Å/sec. It is believed that this portion of the film is representative of a steady-state bulk film etch rate. Both of these parameters, ER and depth, are related to the efficacy of the silylation process, and are considered indicative of a restorative process towards the original film properties.

Table 1 gives a summary of the parameters described above for unpatterned blanket films. The treatments are applied for each silylation compound at a static pressure of 10 Torr at 300° C., for a time period of 1 hour. For the Disclosed molecules 1-3, the depth of repair is about 40% or greater, while the best Comparative molecule (1) repairs only to 26%. Similarly, the Disclosed molecules reduce the bulk ER value by more than 40% over the damaged film. The best Comparative molecule reduces the bulk ER by about 25% over the damaged film. Sample treatments using Comparative molecules 4 and 5 do not show effective repair following the treatment.

TABLE 2

Summary of repair parameters measured following static chemical treatment of damaged low-k films

| Sample | Compound | Depth (%) | ER (Å/s) |
|---|---|---|---|
| As deposited | — | 100 | 0 |
| Plasma damaged | — | 0 | 0.078 |
| Disclosed molecule 1 | TMS pyrrolidine | 46 | 0.039 |
| Disclosed molecule 2 | TMS pyrazole | 42 | 0.038 |
| Disclosed molecule 3 | TMS piperidine | 39 | 0.045 |
| Comp. molecule 1 | HMDS | 26 | 0.059 |
| Comp. molecule 2 | TMSDMA | 23 | 0.073 |
| Comp. molecule 3 | BDMADMS | 5 | 0.058 |
| Comp. molecule 4 | TMS 1,2,4-triazole | 0 | 0.073 |
| Comp. molecule 5 | TMS pyrrole | 0 | 0.060 |

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A method of repairing a dielectric film previously damaged by a processing step(s), the method comprising the step of:

contacting the dielectric film with a repair agent having a formula $R_3SiL$, wherein each R is independently selected from the group consisting of H, methyl, and ethyl; L is a nitrogen-containing ring selected from the group consisting of 1,2,3-triazole, piperidine, 1-methylpiperazine, pyrolidine, and pyrazole; and one nitrogen in the nitrogen-containing ring is bonded directly to the Si atom, whereby the dielectric film is completely or partially restored.

2. The method of claim 1, further comprising heating the dielectric film after introduction into the chamber and prior to introduction of the repair agent.

3. The method of claim 1, further comprising annealing the dielectric film following the reaction contacting step.

4. The method of claim 1, wherein the repair agent is selected from the group consisting of trimethylsilylpyrrolidine, trimethylsilylpyrazole, trimethylsilyl-1,2,3-triazole, trimethylsilylpiperidine, and trimethylsilyl-4-methylpiperazine.

5. The method of claim 4, wherein the repair agent has a total concentration of metal contaminants of less than 10 ppmw.

6. The method of claim 4, wherein the dielectric film is porous.

7. The method of claim 6, wherein the porous dielectric film is nanoporous silica.

8. The method of claim 6, wherein the porous dielectric film has a dielectric constant of 2.0 to 3.0.

9. The method of claim 8, wherein the porous dielectric film has a dielectric constant of 2.2 or smaller.

10. The method of claim 1, wherein the dielectric film comprises a hydrogenated carbon-doped silicon oxide.

11. The method of claim 1, wherein the restoration comprises an improvement of a repair depth and/or a wet etch rate.

12. The method of claim 1, wherein the repair agent is a vapor.

13. The method of claim 1, wherein the repair agent is a liquid.

14. The method of claim 1, wherein the processing step comprises an etching or a chemical mechanical polishing step which removed dielectric film methyl terminations to leave either dangling bonds or Si—OH groups.

15. The method of claim 1, wherein the repair agent is selected from the group consisting of trimethylsilylpyrrolidine, trimethylsilylpyrazole, trimethylsilylpiperidine, and combinations thereof.

* * * * *